US 9,757,528 B2

(12) United States Patent
Rubin

(10) Patent No.: US 9,757,528 B2
(45) Date of Patent: Sep. 12, 2017

(54) NEBULIZER HAVING DIFFERENT NEGATIVE PRESSURE THRESHOLD SETTINGS

(71) Applicant: Darren Rubin, Largo, FL (US)

(72) Inventor: Darren Rubin, Largo, FL (US)

( * ) Notice: Subject to any disclaimer, the term of this patent is extended or adjusted under 35 U.S.C. 154(b) by 627 days.

(21) Appl. No.: 13/969,847

(22) Filed: Aug. 19, 2013

(65) Prior Publication Data

US 2013/0327323 A1    Dec. 12, 2013

Related U.S. Application Data

(63) Continuation-in-part of application No. 12/806,874, filed on Aug. 23, 2010, now abandoned.

(51) Int. Cl.

| | | |
|---|---|---|
| A61M 16/00 | (2006.01) | |
| A61M 15/00 | (2006.01) | |
| B05B 1/26 | (2006.01) | |
| A62B 7/00 | (2006.01) | |
| A61M 11/02 | (2006.01) | |
| A61M 11/06 | (2006.01) | |
| A61M 16/20 | (2006.01) | |
| A61M 16/10 | (2006.01) | |
| A61M 15/02 | (2006.01) | |
| A61M 11/00 | (2006.01) | |

(52) U.S. Cl.
CPC ............ *A61M 11/02* (2013.01); *A61M 11/06* (2013.01); *A61M 15/002* (2014.02); *A61M 15/0085* (2013.01); *A61M 15/0091* (2013.01); *A61M 15/0093* (2014.02); *A61M 16/0093* (2014.02); *A61M 16/1055* (2013.01); *A61M 16/1065* (2014.02); *A61M 16/209* (2014.02); *A61M 11/005* (2013.01); *A61M 15/02* (2013.01); *A61M 16/101* (2014.02)

(58) Field of Classification Search
None
See application file for complete search history.

(56) References Cited

U.S. PATENT DOCUMENTS

| | | | |
|---|---|---|---|
| 2,774,346 A * | 12/1956 | Halliburton ............ | A61M 16/00 128/200.21 |
| 3,732,864 A | 5/1973 | Thompson et al. | |
| 3,989,042 A | 11/1976 | Mitsui et al. | |
| 4,291,688 A | 9/1981 | Kistler | |
| 4,444,202 A | 4/1984 | Rubin et al. | |
| 4,524,769 A | 6/1985 | Wetterlin | |
| 5,054,478 A * | 10/1991 | Grychowski ....... | A61M 16/167 128/200.14 |
| 5,099,833 A * | 3/1992 | Michaels ............. | A61M 16/08 128/200.14 |
| 5,178,138 A | 1/1993 | Walstrom et al. | |

(Continued)

FOREIGN PATENT DOCUMENTS

| | | |
|---|---|---|
| EP | 0471323 A1 | 2/1992 |
| EP | 0653218 A1 | 5/1995 |
| WO | WO-03047763 A1 | 6/2003 |

*Primary Examiner* — Tan-Uyen (Jackie) T Ho
*Assistant Examiner* — Eric Bryant

(57) ABSTRACT

Novel nebulizers and methods are provided for a nebulizer including a dialable negative pressure threshold valve that actuates in response to different negative pressures corresponding to different negative pressure threshold settings of actuation of the valve to influence inhalation effort, aerosol entrainment, and aerosol delivery.

14 Claims, 10 Drawing Sheets

(56) References Cited

U.S. PATENT DOCUMENTS

| | | | | |
|---|---|---|---|---|
| 5,241,954 | A | 9/1993 | Glenn | |
| 5,301,662 | A * | 4/1994 | Bagwell | A61M 16/127 128/200.14 |
| 5,309,900 | A | 5/1994 | Knoch et al. | |
| 5,522,380 | A | 6/1996 | Dwork | |
| 5,596,982 | A | 1/1997 | Blaha-schnabel | |
| 5,875,774 | A | 3/1999 | Clementi et al. | |
| 5,881,716 | A | 3/1999 | Wirch et al. | |
| 5,894,841 | A | 4/1999 | Voges et al. | |
| 6,003,737 | A * | 12/1999 | Mascitelli | B05B 11/0064 222/321.2 |
| 6,044,841 | A * | 4/2000 | Verdun | A61M 11/06 128/200.14 |
| 6,067,984 | A * | 5/2000 | Piper | A61M 16/20 128/204.18 |
| 6,131,570 | A | 10/2000 | Schuster et al. | |
| 6,240,917 | B1 | 6/2001 | Andrade | |
| 6,250,298 | B1 | 6/2001 | Gonda et al. | |
| 6,253,766 | B1 | 7/2001 | Niles et al. | |
| 6,338,443 | B1 * | 1/2002 | Piper | A61M 11/002 128/200.18 |
| 6,425,393 | B1 * | 7/2002 | Lurie | A61H 31/00 128/200.24 |
| 6,539,939 | B2 | 4/2003 | Rubin | |
| 6,595,203 | B1 | 7/2003 | Bird | |
| 6,606,992 | B1 | 8/2003 | Smith et al. | |
| 6,637,430 | B1 | 10/2003 | Voges et al. | |
| 6,655,379 | B2 | 12/2003 | Clark et al. | |
| 6,656,129 | B2 | 12/2003 | Niles et al. | |
| 6,679,250 | B2 | 1/2004 | Walker et al. | |
| 6,708,688 | B1 | 3/2004 | Rubin et al. | |
| 6,718,969 | B1 | 4/2004 | Rubin et al. | |
| 6,776,156 | B2 * | 8/2004 | Lurie | A61M 16/208 128/200.24 |
| 6,904,906 | B2 | 6/2005 | Salter et al. | |
| 6,904,908 | B2 | 6/2005 | Bruce et al. | |
| 6,929,003 | B2 * | 8/2005 | Blacker | A61M 11/06 128/200.24 |
| 6,955,169 | B2 | 10/2005 | Khan | |
| 6,986,349 | B2 * | 1/2006 | Lurie | A61H 31/005 128/202.28 |
| 7,059,582 | B2 | 6/2006 | Adams et al. | |
| 7,073,499 | B1 | 7/2006 | Reinhold et al. | |
| 7,082,947 | B2 | 8/2006 | Smaldone | |
| 7,131,439 | B2 | 11/2006 | Blacker et al. | |
| 7,185,651 | B2 | 3/2007 | Alston et al. | |
| 7,191,780 | B2 | 3/2007 | Faram | |
| 7,201,165 | B2 | 4/2007 | Bruce et al. | |
| 7,204,245 | B2 | 4/2007 | Johnson et al. | |
| 7,329,348 | B2 | 2/2008 | Curello et al. | |
| 7,334,577 | B2 | 2/2008 | Gumaste et al. | |
| 7,347,201 | B2 | 3/2008 | Djupesland | |
| 7,360,536 | B2 | 4/2008 | Patel et al. | |
| 7,472,701 | B2 | 1/2009 | Pfichner et al. | |
| 7,540,286 | B2 | 6/2009 | Cross et al. | |
| 7,559,491 | B1 | 7/2009 | Chang | |
| 7,562,656 | B2 | 7/2009 | Gallem et al. | |
| 7,571,722 | B2 | 8/2009 | Wuttke et al. | |
| 7,581,540 | B2 | 9/2009 | Hale et al. | |
| 7,597,098 | B2 | 10/2009 | Gutsell et al. | |
| 7,600,511 | B2 | 10/2009 | Power et al. | |
| 7,600,512 | B2 | 10/2009 | Lee et al. | |
| 7,621,266 | B2 | 11/2009 | Kladders et al. | |
| 7,624,733 | B2 | 12/2009 | Riley et al. | |
| 7,628,339 | B2 | 12/2009 | Ivri et al. | |
| 7,634,995 | B2 | 12/2009 | Grychowski et al. | |
| 7,655,331 | B2 | 2/2010 | Adams et al. | |
| 7,665,460 | B2 | 2/2010 | Lindsay et al. | |
| 2002/0073995 | A1 * | 6/2002 | Rubin | A61M 15/0086 128/203.14 |
| 2002/0157663 | A1 * | 10/2002 | Blacker | A61M 11/06 128/200.21 |
| 2003/0136399 | A1 * | 7/2003 | Foley | A61M 11/06 128/200.14 |
| 2005/0205085 | A1 * | 9/2005 | Blacker | A61M 11/06 128/200.21 |
| 2005/0247313 | A1 * | 11/2005 | Niles | A61M 11/06 128/203.16 |
| 2007/0023036 | A1 | 2/2007 | Grychowski et al. | |
| 2007/0107719 | A1 * | 5/2007 | Blacker | A61M 11/06 128/200.14 |
| 2007/0227536 | A1 * | 10/2007 | Rivera | A61M 11/06 128/200.21 |
| 2008/0083407 | A1 * | 4/2008 | Grychowski | A61M 11/06 128/200.22 |
| 2009/0020128 | A1 * | 1/2009 | Metzger | A61M 16/0825 128/207.16 |
| 2009/0241945 | A1 * | 10/2009 | Mullner | A61M 16/00 128/202.22 |
| 2011/0114090 | A1 * | 5/2011 | Piper | A61M 11/06 128/200.23 |
| 2013/0276903 | A1 * | 10/2013 | Arcilla | A61M 16/20 137/12 |

\* cited by examiner

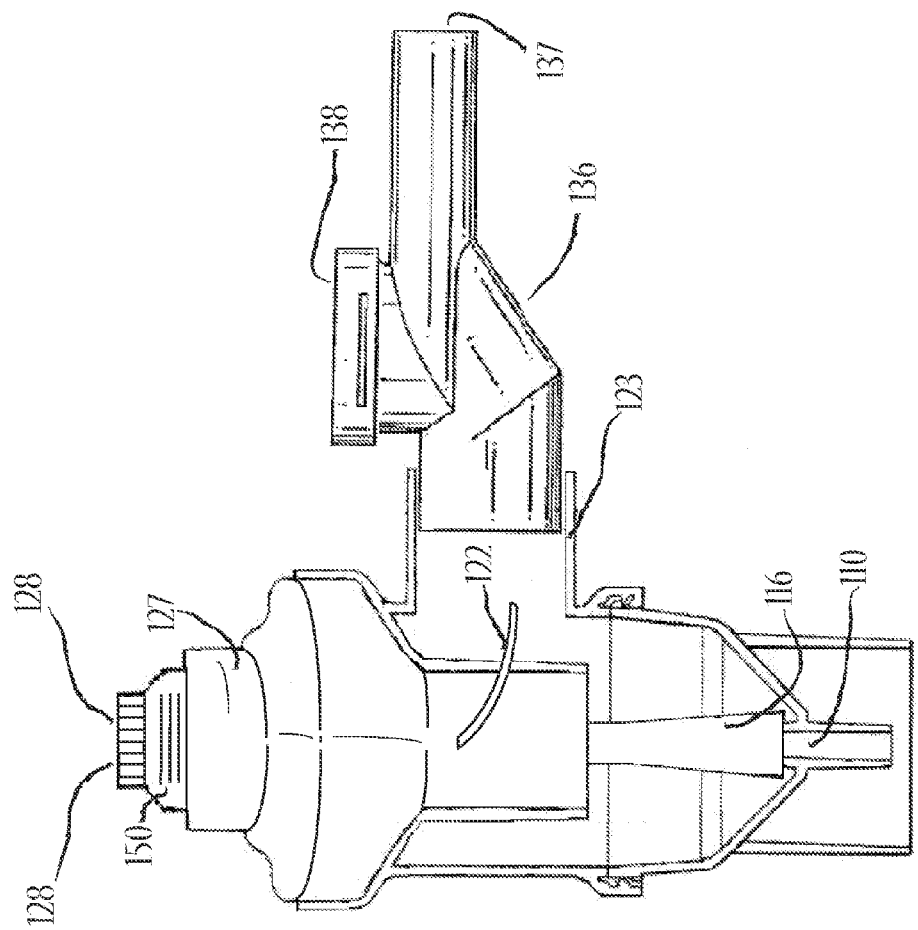
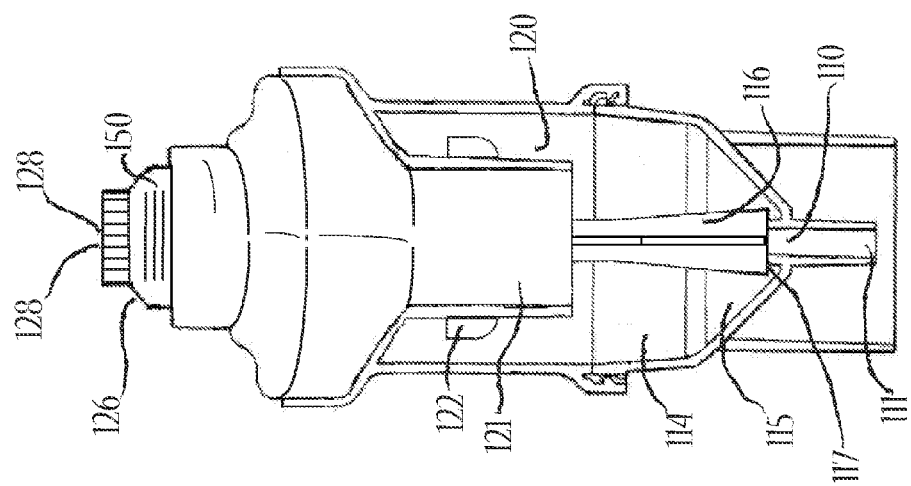

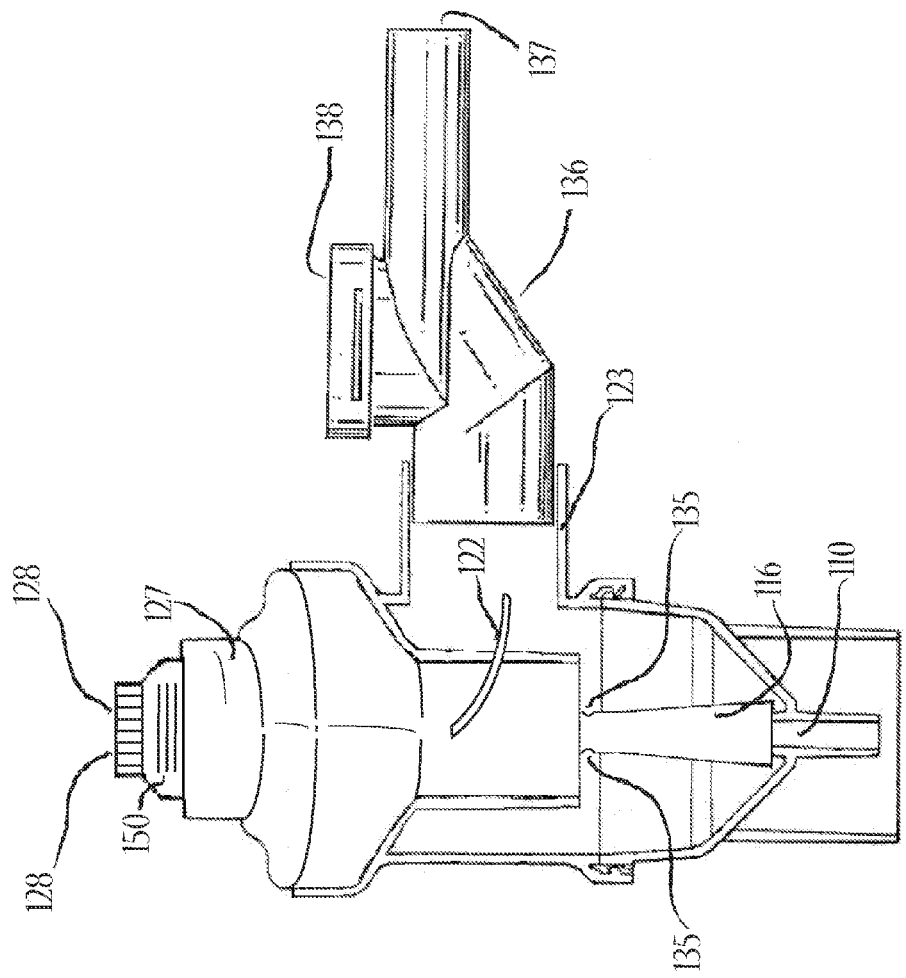
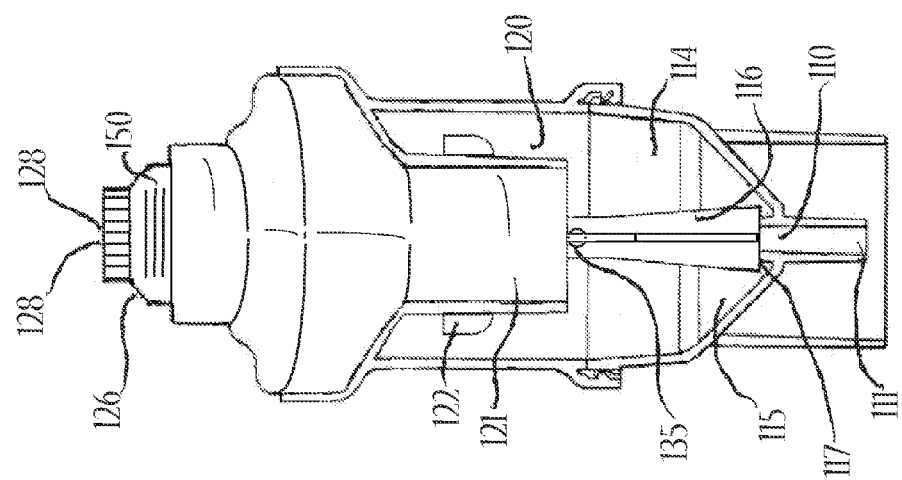
Fig. 9
Fig. 10

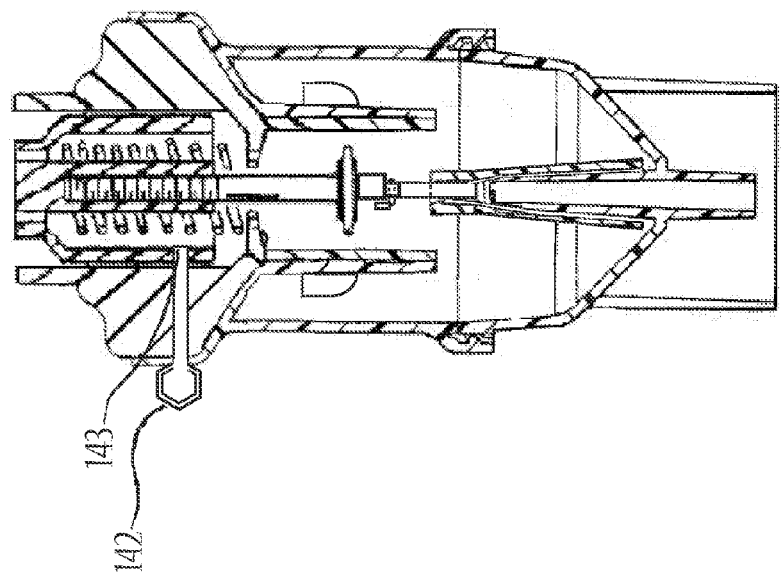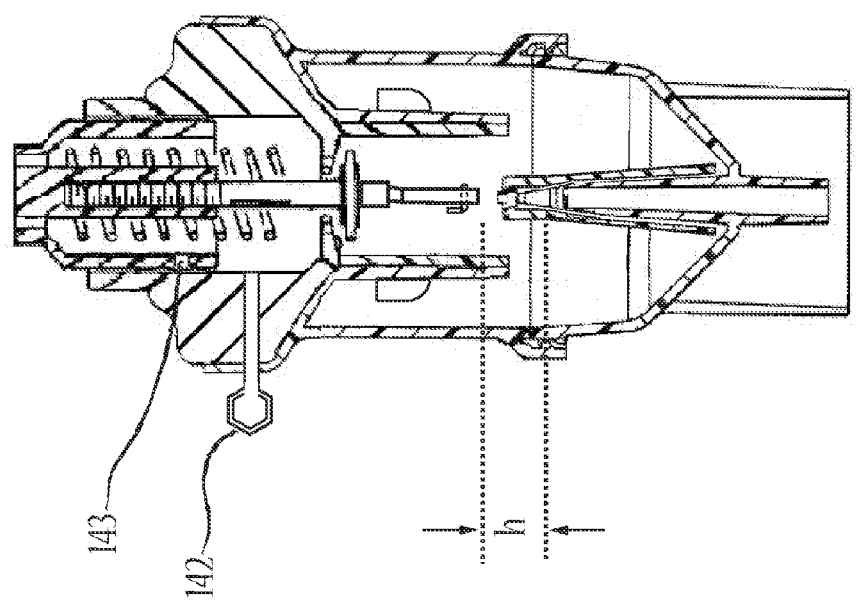

NEBULIZER HAVING DIFFERENT NEGATIVE PRESSURE THRESHOLD SETTINGS

RELATED APPLICATION

This application is a Continuation-In-Part of U.S. patent application Ser. No. 12/806,874 filed on Aug. 23, 2010, which is incorporated herein by reference.

FIELD OF THE INVENTION

The present invention discloses novel nebulizers and methods for varying the degree of negative pressure required and experienced when breathing from a nebulizer. More specifically, embodiments of the present invention relate to nebulizers having different negative pressure threshold settings of actuation of a valve.

BACKGROUND OF THE INVENTION

Nebulizers are medical devices that generate aerosol from a liquid using compressed gas or piezoelectric energy. Jet nebulizers pull liquid from a liquid reservoir and force the liquid, using compressed gas from a tank or air compressor, through a small restricted opening of a jet nozzle cover which causes nebulization. Ultrasonic nebulizers utilize a piezoelectric motor or piezo-oscillating element. Passing liquid through an aperture mesh or membrane that vibrates at ultrasonic frequencies causes nebulization. All nebulizers typically consist of a housing containing a liquid reservoir and a nebulization chamber with a nebulization generating means, e.g., jet nozzle or vibratable mesh, and an aerosol outlet port for receiving a mask or a mouthpiece, either directly or with a T-piece adapter. Some nebulizers are breath-enhanced and may contain ambient air inlets to more efficiently entrain and remove aerosol.

Nebulizers are drug delivery devices when they deliver aerosolized medications to a patient via a mouthpiece, nosepiece, or mask. Nebulizers are primarily used for delivering aerosolized medication, including bronchodilators, for relieving symptoms associated with asthma and chronic obstructive lung disease, COPD. Such asthma and COPD patients often have compromised lung function and trouble breathing. Jet nebulizers are primarily used in the hospital setting for treating these patients. A major drawback to most jet nebulizers, including those requiring a T-piece adapter, is that aerosol is wasted during patient exhalation and aerosol released in the hospital or emergency room can lead to occupational exposure. A large spacer device may be fitted to a nebulizer to help reduce occupational exposure. But a spacer can make delivery inefficient by reducing the concentration of the nebulized bolus, and the spacer does not entrain aerosol from within the nebulizer. A nebulizer can sometimes be fitted with an exhalation filter, which reduces occupational exposure, but does not prevent aerosol waste.

To reduce occupational exposure and aerosol waste during exhalation, a new class of jet nebulizers were developed that coordinated the generation of nebulized aerosols with the breathing cycle. The premise was that nebulization occurred only during inhalation, and not during exhalation. Such nebulizers formed a class known as breath-actuated jet nebulizers. Because these breath-actuated jet nebulizers were primarily intended for treating asthmatics and COPD patients of compromised lung function, and including pediatric patients and those utilizing a mask, they were purposely invented to have a very low triggering point so that normal breathing with no additional inhalation effort is required to actuate nebulization. Otherwise, actuation would be difficult or unattainable by these patients. These breath-actuated jet nebulizers have an actuator having biasing means with a predetermined spring or elastic force that is exceedingly weak. Thus, these prior art breath-actuated jet nebulizers have a very low, constant, single, threshold level of actuation. This threshold level of actuation is so low, that from the patient's perspective, may be considered negligible or insignificant if not associated with an increased inhalation effort that can be experienced. These breath-actuated jet nebulizers lack structures, mechanisms, and dialable interface components that would enable a patient user to increase the threshold level of actuation beyond a minimum baseline level. When and if actuation can be bypassed, there would be no threshold of actuation; breath coordinated actuation does not take place in a continuous nebulization mode.

By way of example, United States Patent Application Number 2007/0023036 to Grychowski et al. describes a breath-actuated nebulizer having a moveable gas diverter located at a variable height above the jet nozzle, which changes a deflection angle of gas emitted from the top of the gas nozzle across the liquid outlet. The gas diverter moves from a nebulizing position to a non-nebulizing position in response to a patient's breathing. Grychowski et al. teaches that a membrane provides an elastic triggering threshold that permits cyclical nebulization to occur that coincides with the breathing of the patient. This threshold is set to fall within normal human breathing parameters so that the diverter moves into and out of proximity with the nozzle top as a result of the patient's normal breathing . . . this level may be approximately less than or equal to 3.0 cm of water. There are no different negative pressure threshold settings of actuation and no dialable means of changing actuation of the device.

By way of another example, U.S. Pat. No. 7,131,439 to Blacker et al. describes a breath-actuated nebulizer having a nozzle cover that moves in response to a patient's breathing. This nozzle cover is associated with an actuator piston that responds to a negative pressure in the range of 0.5 to 1.0 cm of water because Blacker et al. teaches that it is desirable that a nebulizer have adequate sensitivity to quickly respond to an inhalation while not adversely restricting the patient's inhalation. Blacker et al. also teaches a relief piston separately mounted and independently movable with respect to the actuator piston may be used to alleviate inhalation effort after an initial period of inhalation. The relief piston is preferably configured to increase the amount of additional ambient air provided to the chamber as the patient's inhalation increases to keep the negative pressure from rising to a point that makes inhalation difficult for the patient. As such, the relief piston opens to prevent negative pressure from increasing above 1.0 cm of water. The relief piston also has the effect of reducing the resistance to inhalation. Actuation and movement of the actuator piston can be bypassed with a continuous nebulization selection lever, and when in this continuous operation mode, there is no threshold of actuation for nebulization to take place. There are no different negative pressure threshold settings of actuation. Actuation of the actuator piston can only be turned on or turned off, and the negative pressure of the device remains the same; negative pressure is sustained at the same 1.0 cm of water either way.

While these breath-actuated nebulizers serve their intended purpose, they, like regular jet nebulizers, are deficient in being able to increase negative pressure to a different level, and do not have increased negative pressure threshold settings of actuation. It can be appreciated that in certain circumstances, increased negative pressure thresholds and increased inhalation effort can be desirable, and in this sense, the present invention departs from the usual doctrines of effortless asthma and COPD aerosol treatments. For instance, higher negative pressure thresholds, thresholds above 3.0 cm of water, require an increased inhalation effort with greater exertion of the muscles involved in respiration. These higher negative pressure thresholds, as experienced by the patient, can exercise the respiratory muscles beyond what normal breathing can do. Such higher negative pressure thresholds can be used for strength training of the muscles involved in respiration, but can also be used to help maintain lung elasticity and improve respiratory health. Only a nebulizer of the present invention having these different negative pressure threshold settings could be used by chest surgery patients, instead of an incentive spirometer, to help remove secretions and prevent atelectasis on the day of their operation. The present invention may also serve as an incentive device because movement of the negative pressure threshold valve assembly from inhalation may provide a visual signal, and perhaps an auditory signal, to the user. Such a stand-alone nebulizer device has the potential to reduce overall hospital costs, while saving time and providing greater convenience. The prior art nebulizers of Grychowski et al. and Blacker et al. are not capable of providing negative pressure threshold resistance training because they have a negative pressure threshold that is exceedingly low and does not require an increased inhalation effort from the patient. Their nebulizers also cannot make inhalation more difficult than normal breathing, and therefore, lack the therapeutic benefits associated with an increased negative pressure threshold.

For patients with adequate lung function that can achieve greater inhalation effort, the different negative pressure threshold settings of this novel nebulizer can have profound effects on aerosol delivery dynamics. More specifically, by having actuation of nebulization and aerosol entrainment associated with different negative pressure threshold settings, the nebulizer can be used to selectively target aerosols to one or more different airway regions. In effect, aerosol actuation, entrainment, and delivery occur when one or more different airways are optimally expanded with the desired pressure for enhanced drug targeting and delivery efficiency.

More pharmaceuticals are being made available for inhalation. This includes pharmaceuticals that can be delivered to the systemic circulation via the pulmonary route. As an improved drug delivery device, the present invention can improve the delivery dynamics and targeting of these drugs. Selective targeting of aerosols to one or more different airway regions can aid in the targeting of aerosolized chemotherapies against lung cancer. Selective targeting of aerosols to one or more different airway regions can also have profound military medicine applications, including biodefense to counter bioterrorism, by coating upper airways with antibiotics against anthrax or other infectious agents, or by providing anticholinergic agents to the systemic circulation via alveoli as an antidote to nerve agent exposure. The present invention also has the potential to enhance the deliverability of drug candidates in development, which has the potential to reduce drug development costs.

Accordingly, there is a need for an improved nebulizer that can overcome one or more of the limitations discussed above, and open the way for new and improved methods of providing nebulization treatments.

SUMMARY OF THE INVENTION

Therefore, various exemplary embodiments of the invention may provide an improved nebulizer having different negative pressure thresholds. The embodiments of this novel nebulizer generally include an adjustable negative pressure threshold valve that actuates in response to different negative pressures corresponding to different negative pressure threshold settings of actuation. Such a nebulizer is only embodied and described by the present invention. The negative pressure threshold valve generally includes a biasing member component having a variable biasing member force. More specifically, the negative pressure threshold valve of preferred embodiments includes a dialable component with settings that change the pressure thresholds of actuation, by changing the biasing member force of the biasing member. These embodiments enable the patient user to increase the negative pressure threshold required for actuation to take place so that actuation of the valve is associated with an increased inhalation effort experienced by the patient.

To attain the advantages and in accordance with the purpose of the invention, as embodied and broadly described herein, one exemplary aspect of the invention provides a novel jet nebulizer that includes a dialable negative pressure threshold valve whereby actuation of this valve, at any of the different negative pressure threshold settings, is associated with allowing ambient air to enter through the nebulizer, preferably by the valve including at least one ambient air inlet of the nebulizer, so that aerosol can be entrained from within the nebulizer.

Accordingly, this first exemplary nebulizer embodiment is adapted to nebulize/atomize a liquid substance/solution for inhalation using compressed/pressurized gas, and comprises: a liquid reservoir container defining an inner space adapted to receive a liquid therein, a non-moveable jet nozzle provided through at least some of the inner space for passage of a pressurized gas entering from a gas inlet and exiting through a tapered air outlet at the jet nozzle tip, a non-moveable jacket circumferentially sleeved around the jet nozzle to define a constant fluid-introducing gap there between, the fluid-introducing gap being in fluid communication with the inner space for passage of the liquid there through, the jacket having at least one restricted opening at its tip which emits the jet, a mist-discharging conduit extending into the nebulization chamber and in fluid communication with the inner space for passage of a mist there through and aligned with the jacket in a jet-ejecting direction, an impact baffle positioned in the path of the jet to disperse nebulized particles generated as high-pressure gas atomizes the liquid leaving the restricted opening of the jacket tip, at least one aperture for the mist-discharging conduit to receive ambient air, and an aerosol air outlet port for delivering aerosol to the airways of a patient.

The nebulizer further includes an adjustable negative pressure threshold valve operatively coupled to a nebulization chamber. The chamber and its mist-discharging conduit or chimney are adapted to receive both nebulized aerosol particles and ambient air.

The adjustable negative pressure threshold valve has a plurality of settings of actuation. The nebulizer further includes a reciprocable component operatively coupled to the adjustable negative pressure threshold valve, the reciprocable component is adapted to adjust the settings of actuation of the adjustable negative pressure threshold valve. The reciprocable component is comprised of a rotatable cap with an integrally formed cylindrical wall slidably received through a preferably cylindrical upper region of the device housing. The rotatable cap includes one set of ambient air inlets at the top base of the cap.

The rotatable cap further includes a tubular guide extending through a portion of it, the tubular guide includes female threads designed to receive the male threads of a thin rod comprising a component of the valve so that the reciprocal component is operatively coupled to the valve. The threaded thin rod further includes a circular disc fixedly attached to the bottom of the rod, the circular disc and rod comprises an actuator piston of the threshold valve. The circular disc is located within the interior chamber of the device, and preferably within a chimney region of the device having a Venturi-like central aperture between the disc and the rotatable cap.

A load calibrated, coiled spring biasing member further comprises the valve and is positioned inside of the rotatable cap around the tubular guide and thin rod. The spring biasing member puts upward pressure on the rotatable cap so that the circular disc is pulled against the top surface of the inner chamber chimney to block the central aperture and prevent ambient air from entering the central aperture before actuation of the valve takes place.

The spring has an adjustable biasing member force that is modulated by rotation of the cap so that the distance that the thin rod screws into the tubular guide of the cap changes, thereby affecting the space between the cap and the central aperture of the chimney, and thereby changing the compression and tension of the spring and changing the negative pressure threshold required for actuation of the valve. In this manner, the reciprocable component is adapted to adjust the settings of actuation of the adjustable negative pressure threshold valve by changing the biasing member force of the biasing member component.

The adjustable negative pressure threshold valve is adapted to actuate in response to different negative pressures corresponding to different negative pressure threshold settings of actuation. The valve actuates when a sufficient negative pressure is generated by patient inhalation to surpass the biasing member force of the spring, so that the actuator piston moves downward. Downward movement of the actuator piston allows ambient air to enter the central aperture of the device; ambient air coming from the ambient air inlet of the reciprocable component of the valve. The reciprocable component and the valve are adapted to influence nebulized aerosol delivery by allowing ambient air to enter the nebulization chamber and entrain aerosol particles.

Actuation of the valve ceases when negative pressure generated by the patient decreases below the negative pressure threshold of the valve, and the actuator piston and valve returns to its resting position.

To attain the other advantages and in accordance with the purpose of the invention, as embodied and broadly described herein, another exemplary aspect of the invention provides a novel jet nebulizer that includes a dialable negative pressure threshold valve whereby actuation of this valve, at any of the different negative pressure threshold settings, is also associated with actuation of nebulization so that nebulization is coordinated with the patient's breathing cycle. To achieve non-continuous, breath activated nebulization that is coordinated with the patient's breathing cycle, the nebulizer according to an exemplary embodiment of the invention is further adapted and modified.

Accordingly, this modified first exemplary nebulizer embodiment is adapted to nebulize/atomize a liquid substance/solution for inhalation using compressed/pressurized gas, and comprises: a liquid reservoir container defining an inner space adapted to receive a liquid therein, a non-moveable jet nozzle provided through at least some of the inner space for passage of a pressurized gas entering from a gas inlet and exiting through a tapered air outlet at the jet nozzle tip, a non-moveable jacket circumferentially sleeved around the jet nozzle to define a constant fluid-introducing gap there between, the fluid-introducing gap being in fluid communication with the inner space for passage of the liquid there through, the jacket having at least one restricted opening at its tip which emits the jet, a mist-discharging conduit extending into the nebulization chamber and in fluid communication with the inner space for passage of a mist there through and aligned with the jacket in a jet-ejecting direction, an impact baffle positioned in the path of the jet to disperse nebulized particles generated as high-pressure gas atomizes the liquid leaving the restricted opening of the jacket tip, at least one aperture for the mist-discharging conduit to receive ambient air, and an aerosol air outlet port for delivering aerosol to the airways of a patient.

The jacket further includes the modification of at most two small holes at its tip, adjacent to the restricted opening. When the at most two small jacket holes are unobstructed, nebulization does not take place so that aerosol is not generated from the jacket restricted opening.

The nebulizer further includes an adjustable negative pressure threshold valve operatively coupled to a nebulization chamber. The chamber and its mist-discharging conduit or chimney are adapted to receive both nebulized aerosol particles and ambient air.

The adjustable negative pressure threshold valve has a plurality of settings of actuation. The nebulizer further includes a reciprocable component operatively coupled to the adjustable negative pressure threshold valve, the reciprocable component is adapted to adjust the settings of actuation of the adjustable negative pressure threshold valve. The reciprocable component is comprised of a rotatable cap with an integrally formed cylindrical wall slidably received through a preferably cylindrical upper region of the device housing. The rotatable cap includes one set of ambient air inlets at the top base of the cap.

The rotatable cap further includes a tubular guide extending through a portion of it, the tubular guide includes female threads designed to receive the male threads of a thin rod comprising a component of the valve so that the reciprocal component is operatively coupled to the valve. The threaded thin rod further includes a circular disc fixedly attached to the bottom of the rod, the circular disc and rod comprises an actuator piston of the threshold valve. The circular disc is located within the interior chamber of the device, and preferably within a chimney region of the device having a Venturi-like central aperture between the disc and the rotatable cap.

The nebulizer further includes the modification of a moveable seal associated with the actuator piston. The moveable seal is preferably horseshoe-shaped and is not a component of the nozzle jacket. The moveable seal is attached under the circular disc, and preferably attached to the end of thin rod, a portion of the rod which extends past the circular disc.

A load calibrated, coiled spring biasing member further comprises the valve and is positioned inside of the rotatable cap around the tubular guide and thin rod. The spring biasing member puts upward pressure on the rotatable cap so that the circular disc is pulled against the top surface of the inner chamber chimney to block the central aperture and prevent ambient air from entering the central aperture before actuation of the valve takes place.

The spring has an adjustable biasing member force that is modulated by rotation of the cap so that the distance that the thin rod screws into the tubular guide of the cap changes, thereby affecting the space between the cap and the central aperture of the chimney, and thereby changing the compression and tension of the spring and changing the negative pressure threshold required for actuation of the valve. In this manner, the reciprocable component is adapted to adjust the settings of actuation of the adjustable negative pressure threshold valve by changing the biasing member force of the biasing member component.

The adjustable negative pressure threshold valve is adapted to actuate in response to different negative pressures corresponding to different negative pressure threshold settings of actuation. The valve actuates when a sufficient negative pressure is generated by patient inhalation to surpass the biasing member force of the spring, so that the actuator piston moves downward. Downward movement of the actuator piston allows ambient air to enter the central aperture of the device; ambient air coming from the ambient air inlet of the reciprocable component of the valve. Downward movement of the actuator piston during actuation also moves the moveable seal downward to flank and obstruct the at most two small holes at the tip of the nozzle jacket, adjacent to the restricted opening, so that nebulization takes place while sufficient negative pressure is generated during inhalation. The reciprocable component and the valve are adapted to influence nebulized aerosol delivery by allowing ambient air to enter the nebulization chamber and entrain aerosol particles when nebulization is actuated.

Actuation of the valve ceases when the negative pressure generated by the patient decreases below the negative pressure threshold of the valve. As inhalation ends, the actuator piston of the valve and its associated moveable seal return to their resting position, so that the at most two small jacket holes are unobstructed again and nebulization stops. Nebulization is therefore coordinated with the patient's breathing cycle.

The mechanism of breath activation of the present invention is much different from Grychowski et al. and Blacker et al, which are more susceptible to variations in nebulized particle generation and aerosol particle mass median aerodynamic diameter, MMAD, attributed to minor differences in movement of nebulization components. Unlike Grychowski et al., there is no moveable gas diverter located above the jet nozzle, which changes a deflection angle of gas emitted from the top of the gas nozzle across the liquid outlet. Unlike Blacker et al., there is no moveable nozzle cover or moveable portion of a nozzle cover that can result in variability in a fluid introducing gap between the jet nozzle and nozzle cover, and disturb the liquid medicament layer. The present invention preferably has a jet nozzle, a nozzle cover, and an impact baffle that do not move and are always in a fixed position relative to each other. Therefore, when nebulization takes place, the aerosol particles generated by the present invention are always consistent in MMAD. Also unlike the prior art, ambient air cannot flow through the present device before actuation takes place. This permits the present invention to build up enough negative pressure to overcome the substantial resistance associated with the dialable negative pressure threshold valve. Only the present invention has multiple settings with different negative pressure thresholds associated with each. The biasing member force of the present invention is not predetermined as the prior art, and instead changes in accordance to these negative pressure threshold settings of actuation. Each different setting is consistent, sustained, and reproducible so that the dialable valve of the present invention serves as a calibrated negative pressure threshold control element.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments consistent with the invention, and, together with the description, serve to explain the principles of the invention.

FIG. 1 is a back view of a nebulizer according to an exemplary embodiment of the invention including a dialable negative pressure threshold valve with settings that increase the negative pressure threshold required to actuate the valve and allow ambient air to enter the device for enhanced aerosol entrainment and delivery. Nebulization is continuously generated. The nebulizer is shown with valve in a non-actuated state. In contrast to the modified nebulizer shown in FIG. 9, no small jacket hole accompanies the jacket's restricted opening.

FIG. 2 is a side view of the nebulizer shown with valve in a non-actuated state. In contrast to the modified nebulizer shown in FIG. 10, no small jacket hole accompanies the jacket's restricted opening.

FIG. 9 is a back view of a modified nebulizer according to an exemplary embodiment of the invention that is capable of non-continuous, breath activated nebulization that is coordinated with the patient's breathing cycle. The modified nebulizer is shown in a non-actuated state. The modification of at most two small jacket holes 135 at the tip of the jacket is directly visible from this view, although a joint that fuses the jacket 116 to the chimney 121 structure is shown in front of a portion of this hole 135.

FIG. 10 is a side view of the modified nebulizer in a non-actuated state. The modification of at most two small jacket holes 135 at the tip of the jacket is visible as a profile from this view.

FIG. 15 is a cross-sectional back view of a nebulizer that is further modified and includes a valve bypass lock pin 142 and dial lock pin port 143. This further modified nebulizer is shown unlocked in a non-actuated state.

FIG. 16 is a cross-sectional back view of the nebulizer that is further modified and shown with valve bypass lock pin 142 set into dial lock pin port 143. The valve has been bypassed and locked so that nebulization is continuous without any actuation threshold.

DESCRIPTION OF THE PRESENTLY PREFERRED EMBODIMENTS

Reference will now be made in detail to exemplary embodiments consistent with the present invention, examples of which are illustrated in the accompanying drawings. Wherever possible, the same reference numbers will be used throughout the drawings to refer to the same or like parts.

FIGS. 1-8 show an exemplary jet nebulizer according to the present invention that includes a dialable negative pressure threshold valve whereby actuation of this valve, at any of the different negative pressure threshold settings, is associated with allowing ambient air to enter through the nebulizer, preferably as the valve includes at least one ambient air inlet of the nebulizer, for enhanced aerosol entrainment and delivery.

Figure 4:
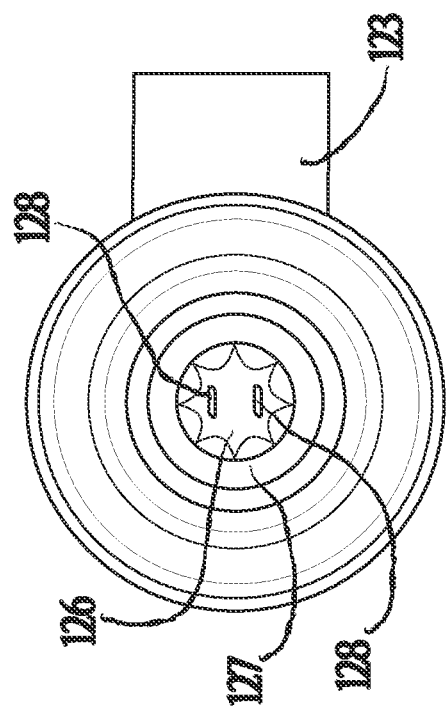
FIG. 4 is a top down view of the nebulizer. The rotatable cap 126 of the negative pressure threshold valve assembly is shown fitted into the cylindrical upper region of the device housing 127. Ambient air inlets 128 are shown at the top of the cap. The rotatable cap is a dialable user interface with finger grooves shown for easy gripping when changing the negative pressure threshold settings of actuation. A mouthpiece is not shown.
Figure 3:
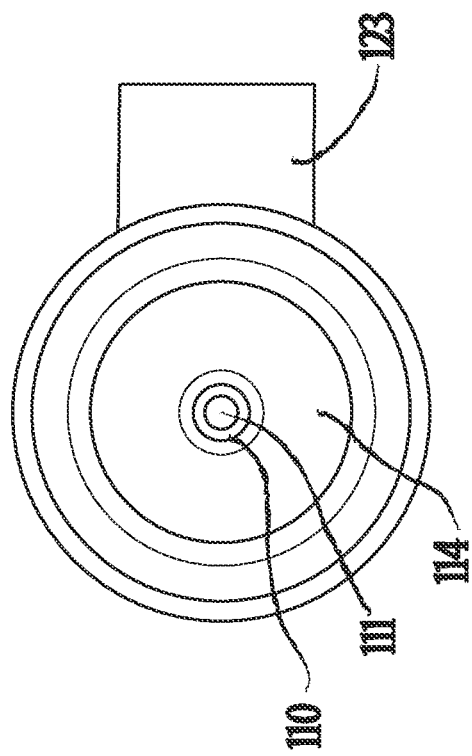
FIG. 3 is a bottom up view of the nebulizer. The bottom of the jet nozzle 110 and its compressed gas inlet 111, along with the bottom of liquid reservoir container 114, are visible. A mouthpiece is not shown.
Figure 5:
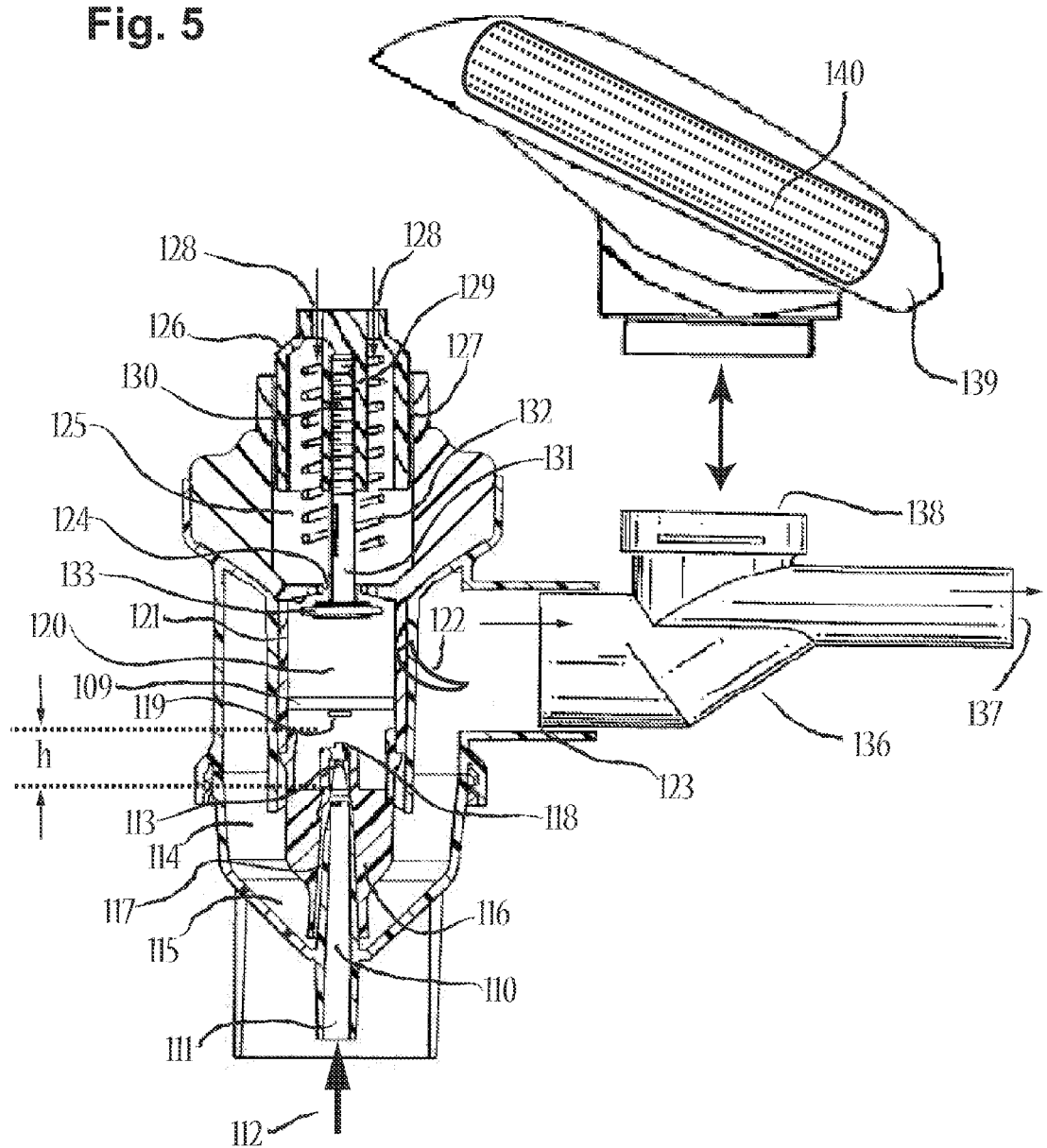
FIG. 5 is a cross-sectional side view of the nebulizer shown in a non-actuated state. In contrast to the modified nebulizer shown in FIG. 11, no moveable seal 134 is attached to the actuator piston of the valve.
Figure 6:
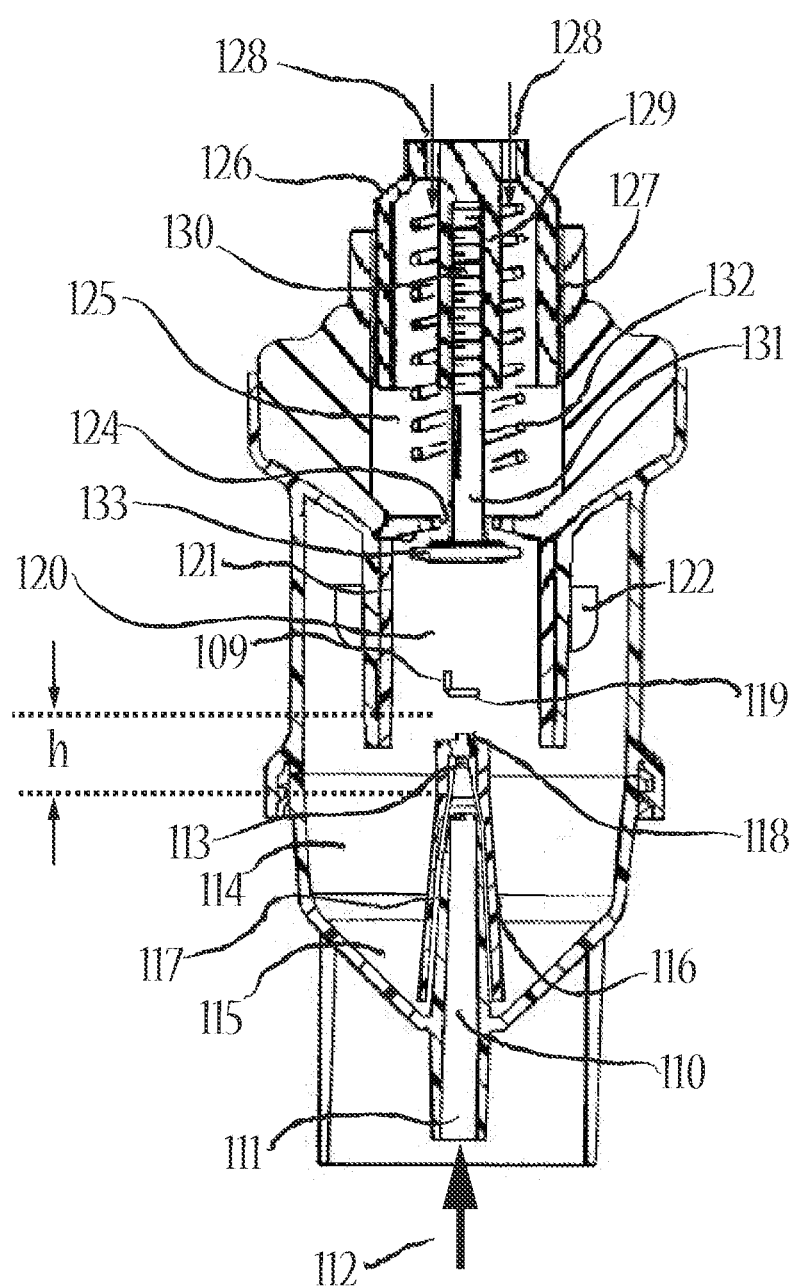
FIG. 6 is a cross-sectional back view of the nebulizer shown in a non-actuated state. In contrast to the modified nebulizer shown in FIG. 12, no moveable seal 134 is attached to the actuator piston of the valve.

Referring now to the cross-sectional views, FIG. 5 side view and FIG. 6 back view, this exemplary jet nebulizer is shown including a jet nozzle 110 able to receive compressed air and/or compressed oxygen from compressed gas inlet 111 connected to a source of compressed gas 112. Sources of compressed gas can may include air pumps, portable air compressors, oxygen concentrators, or pressurized medical gas tanks. When the embodiment serves as a disposable nebulizer, oxygen tubing, not shown, connects gas inlet 111 to sources of compressed gas 112. A gas flowmeter may also be connected in this gas circuit. When the embodiment serves as a hand-held, non-disposable nebulizer, the source of compressed gas 112 may even be a component of the device itself when the source of compressed gas is a built-in miniature, battery powered, air compressor.

Jet nozzle 110 includes a tapered air outlet 113 at the top of its conical tip pointing upward. A portion of the jet nozzle 110 resides inside of a liquid reservoir container 114, defining an inner space adapted to receive a liquid therein and filled with a liquid medicament formulation 115. The reservoir container 114 is connected detachably and securely to the main device housing. A jacket 116 is circumferentially sleeved around the jet nozzle to define a fluid-introducing gap 117 therebetween. The exterior surface of the jet nozzle or the interior surface of the jacket can be smooth, irregular, or grooved. When assembled, this jacket is fixedly positioned over the jet nozzle and does not move so that the fluid-introducing gap is held constant. At the top of the tip of the jacket is at least one restricted opening 118, which faces upward and is aligned with the nozzle air outlet 113. When in use, a high-pressure air jet passes through the jet nozzle 110, from its gas inlet 111 and out through its tapered air outlet 113, and out through restricted opening 118 of the jacket tip. As liquid from the fluid-introducing gap 117 is brought into the jet, high-pressure air atomizes the liquid as the liquid leaves the restricted opening 118 of the jacket tip.

Many of the particles produced are coarse droplets above 15 micrometers in size. Because aerosol particles of a MMAD of under 5 micrometers, and preferably under 2 micrometers, are more desirable for inhalation, an impact baffle 119 can be placed above the jacket. Large particles collide with the impact baffle, causing them to condense into liquid and return to the reservoir, so that only smaller sized aerosol particles are available for inhalation. Baffling also effects how much aerosol is released rather than returned to the reservoir, and thus, effects efficiency of the nebulizer. The size and position of the impact baffle is chosen for the desired particle size and quantity of aerosol bolus desired. Impact baffle 119 is shown held permanently in place a certain distance above the jet nozzle by a horizontal structural beam 109 that is attached to the walls of a conical section or chimney 121 contained in the interior nebulization chamber 120. Chimney 121 is a mist discharging conduit that extends downward and is in fluid communication with the inner space for passage of a mist there through and aligned with the jacket in a jet-ejecting direction. Jacket 116 may be adjoined to chimney 121 by a joint region, which is shown but not numbered in the drawings. Extension guides 122 may protrude from the walls of the chimney 121. Chimney 121 and its extension guides 122 also prevent undesirable, larger droplets from exiting the device, and instead, cause such droplets to condense and return to the liquid reservoir 114. In this manner, smaller particles with a MMAD ideal for inhalation are able to freely exit the device through aerosol air outlet port 123. Furthermore, chimney 121 and its extension guides 122 cause ambient air entering the device to take a more tortuous flow path through the device to ensure that an adequate amount of aerosol is entrained in this airflow to reduce particle size and/or to prevent particles from colliding and growing. Extension guides 122 of the chimney 121, or other baffles residing in the device, may be curved or spiral-shaped to cause cyclonic action of aerosol entrained airflow.

Ambient air enters interior chamber 120 through a Venturi-like central aperture 124 located at the top of chimney 121. Airflow through this central aperture 124 is regulated by a negative pressure threshold valve assembly 125. The negative pressure threshold valve assembly is comprised of a rotatable cap 126 with an integrally formed cylindrical wall slidably received through the cylindrical upper region of the device housing 127. One or more ambient air inlets 128 are found at the top of rotatable cap 126. The rotatable cap also has a tubular guide 129 extending through a portion of it. The tubular guide has female threads 130 designed to receive the male threads of a thin rod 131. A load calibrated, coiled spring 132, or other resilient biasing member, is positioned inside of the rotatable cap 126, around the tubular guide 129 and thin rod 131. A circular disc 133, along thin rod 131, is located within the interior chamber 120 of the device, and together circular disc and thin rod comprise the actuator piston of threshold valve 125. As the spring 132 biasing member puts upward pressure on rotatable cap 126, circular disc 133 is pulled against the top surface of inner chamber 120, or chimney 121, and thus, blocks central aperture 124. The blocking of ambient air into the nebulization chamber allows significant negative pressure to efficiently be reached prior to actuation.

Figure 7:
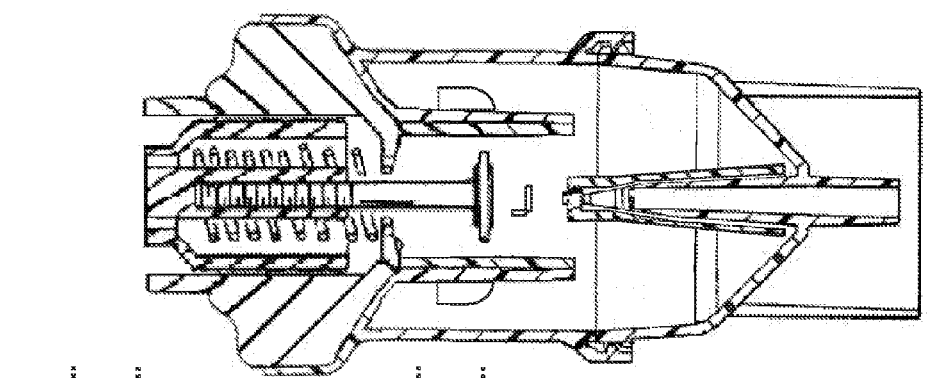
FIG. 7 is a cross-sectional back view of the nebulizer illustrating the adjustable negative pressure threshold valve according to an exemplary embodiment of the invention in a non-actuated state while nebulization is continuously generated. The entire jacket 116 is fixed in position over the jet nozzle 110.
Figure 8:
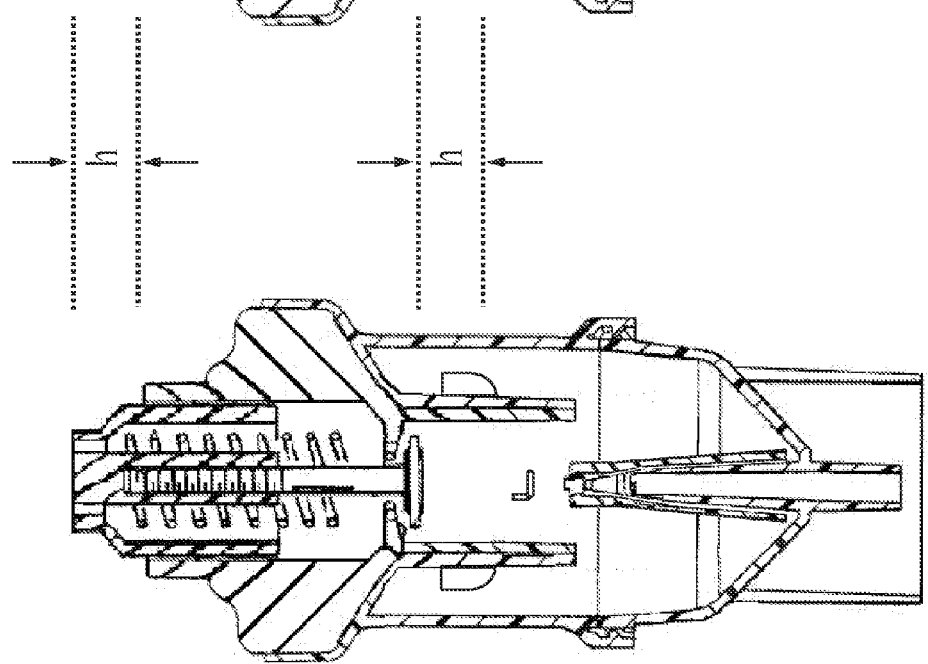
FIG. 8 is a cross-sectional back view of the nebulizer illustrating the adjustable negative pressure threshold valve according to an exemplary embodiment of the invention in a fully actuated state to allow ambient air to enter after having moved a distance of "h" downward. Nebulization is continuously generated. The entire jacket 116 remained fixed in position over the jet nozzle 110.

FIG. 7 shows the cross-sectional, back view of the nebulizer with its negative pressure threshold valve in a non-actuated state, while FIG. 8 shows this same view of the nebulizer with its valve in an actuated state. The entire jacket 116 is comprised of a single piece and always remains fixed in position over the jet nozzle 110 whether the valve is actuated or not. During inhalation, when the negative pressure inside the nebulizer, distributed over the bottom surface of circular disc 133 of the actuator piston of the valve assembly, exceeds the biasing member force or spring force of coiled spring 132, the threshold valve will actuate as the spring compresses and the actuator piston moves down. If pressurized air is being supplied to the nebulizer via compressed gas inlet 111, then in order to generate sufficient negative pressure within the nebulizer, the rate of airflow exiting the nebulizer should generally exceed the pressurized gas flow rate entering the nebulizer chamber.

When the valve is actuated, ambient air enters the device through ambient air inlets 128, entrains nebulized particles, and carries these particles out of the device through aerosol air outlet port 123. Although actuation of the threshold valve in this current configuration does not influence the generation of nebulized particles, actuation does influence entrainment of these particles so that the jet nebulizer serves as a breath actuated aerosol entrainment device, which is different from breath actuated nebulization. Referring to FIGS. 1-2, calibrating indicia 150 are provided on the exterior cylindrical walls of rotatable cap 126, so that negative pressure threshold valve 125 also serves as a calibrated pressure threshold control element having different settings. The adjustable negative pressure threshold valve includes a plurality of negative pressure settings of actuation. The different negative pressure threshold settings of actuation are preferably incremental, although the differences in negative pressure among the settings can also be exponential instead of linear, or a combination of exponential and linear differences among the settings. Serving as a dialable user interface, or dial, the rotatable cap preferably has grooves or ridges on its exterior surface, shown in FIG. 4, for easy gripping and turning with a patient's fingers. Referring to FIG. 5, as the cap is rotated as a dial to a different setting, the distance that the thin rod 131 screws into the tubular guide 129 of the cap also changes, thereby affecting the space between the cap and the central aperture 124 of the device housing 127, and thus, changing the compression of the spring 132 and changing the biasing member force of this biasing member. By varying the tension of the spring, one can control the negative pressure threshold required for actuation of this dialable negative pressure threshold valve. Negative pressure actuation thresholds above 1 centimeter of water, and preferably above 3 centimeters of water, can be achieved by changing to increasingly greater negative pressure threshold settings of the dialable valve. Negative pressure threshold settings of actuation could conceivably range past 10 centimeters of water, range past 20 centimeters of water, range past 50 centimeters of water, or even range past 100 centimeters of water, and upper range examples are not meant to be limiting. In other words, the upper range limit can be well under a negative pressure threshold that is humanly impossible to reach or at a negative pressure threshold that is humanly impossible to reach.

Preferably, it is desirable to maintain the valve in its actuated state throughout most of inhalation. This would require the patient to provide a sustained negative pressure equal to or above the threshold required by the negative pressure threshold setting of the valve. The maintaining of a sustained negative pressure over time can provide for a sustained maximal inhalation.

Expansion of the lungs is what generates negative pressure associated with inhalation. In order for a patient to generate a sufficient negative pressure needed for actuation and sustained actuation of a difficult threshold setting, the muscles involved in respiration, including the diaphragm, must contract strong enough to enlarge the thoracic cavity, and expand the lungs, sufficiently enough and for as long as possible. Any resistance associated with a negative pressure threshold that requires an increased inhalation effort from the patient is also a resistance to the contraction of the muscles involved in respiration in expanding the lungs. This is a significant physiological effect because it can be detected and experienced by the patient.

It can be appreciated that in certain circumstances, increased negative pressure thresholds can provide desirable therapeutic benefits. For instance, higher negative pressure thresholds, thresholds above 3.0 cm of water, require an increased inhalation effort with greater exertion of the muscles involved in respiration. These higher negative pressure thresholds, as experienced by the patient, can exercise the respiratory muscles beyond what normal breathing can do. Such higher negative pressure thresholds can be used for strength training of the muscles involved in respiration, but can also be used to help maintain lung elasticity and improve respiratory health. Only a nebulizer of the present invention having these different negative pressure threshold settings could be used by chest surgery patients, instead of an incentive spirometer, to help remove secretions and prevent atelectasis on the day of their operation. Such a stand-alone nebulizer device has the potential to reduce overall hospital costs, while saving time and providing greater convenience. Only the present invention discloses a stand-alone nebulizer that can provide effective negative pressure threshold resistance training that can be performed before, after, or simultaneously with nebulized aerosol delivery. Clear and expanded lungs and airways are also more receptive to receiving delivered aerosol. The present invention departs from the usual doctrines of effortless aerosol treatments to demand substantially more inhalation effort from the patient.

Referring to FIG. 5 again, a user mouthpiece 136 attaches to device outlet, aerosol air outlet port 123. Various nebulizer mouthpieces have been described in the art. Airflow passes through the mouthpiece and out through its outlet 137. Said mouthpiece may contain an exhaust port 138, containing an elastomeric one-way, flap, valve, which vents user exhalation, but does not open during user inhalation. Therefore the one-way flap valve does not have any influence on the negative pressure of the nebulizer during inhalation or on the patient's ability to generate negative pressure during inhalation. An optional and/or removable filter housing assembly 139 may be aligned with exhaust port 138, to allow exhaled air to pass through a filter element 140, and out of the filter housing 139. A preferred filter element 140 may be a 3M filtrate filter, or other HEPA filter, able to capture infectious particles and aerosol particles larger than 0.3 micrometers in diameter from exhalation, thereby preventing cross contamination to nearby individuals. A contaminated filter element may be cleaned or replaced as necessary.

The exemplary jet nebulizer according to the present invention has a variable negative pressure threshold valve that actuates in response to different negative pressures corresponding to different negative pressure threshold settings of actuation. The negative pressure threshold valve is adjustable and includes a biasing member component of the valve, the valve further including settings that change the negative pressure thresholds of actuation of the valve by changing the biasing member force of the biasing member component of the valve. The valve is able to influence nebulized aerosol delivery and allow ambient air to enter and entrain aerosol particles.

This exemplary nebulizer can include additional components or modifications so that the efficiency of nebulization can be adjusted. For example, FIGS. 5-8 show the impact baffle 119 held in a fixed position above the jet nozzle by horizontal support beam 109. If the horizontal support beam was located higher in the chimney, the impact baffle would be a further distance from the jet nozzle. Adjustments in baffling can affect the ratio of large to small aerosol particles generated and released, also having effects on aerosol bolus size and nebulizer efficiency. The horizontal support beam could also serve the purpose of an obstruction to limit how far down the actuator piston, disc 133 and rod 131, moves down when actuated. In other examples, instead of there being a horizontal support beam 109, the impact baffle could instead be attached to the bottom of circular disc 133 or some other structure emanating from rod 131, so that the impact baffle 119 is variably positioned above the jet nozzle in association with movement of the actuator piston. Such an example can allow for a continuous, but non-constant, aerosol output, so that aerosol bolus size changes throughout the inhalation cycle. In other examples, the impact baffle 119 may not be present, or circular disc 133 can also serve the function of an impact baffle. These other examples of variable impact baffles are not shown, but may be implemented. Also, these examples are not meant to be limiting.

FIGS. 1-8 show the exemplary nebulizer invention as a jet nebulizer that continuously nebulizes as long as pressurized gas is being supplied to jet nozzle inlet 111, and as long as the liquid reservoir container 114 is filled with a liquid medicament 115. Additional components and modifications of this exemplary nebulizer can be included so that nebulization is not continuous.

FIGS. 9-14 show another exemplary aspect of the jet nebulizer according to the present invention that is modified and includes a dialable negative pressure threshold valve whereby actuation of this valve, at any of the different negative pressure threshold settings, is also associated with actuation of nebulization so that nebulization is coordinated with the patient's breathing cycle. Nebulization is thus non-continuous and breath activated in this modified nebulizer that serves as a breath actuated nebulization device.

Referring now to the back and side views of FIGS. 9-10, this exemplary jet nebulizer is shown modified by including one to two small jacket holes 135, at the tip of the jacket adjacent to the restricted opening 118. Small jacket hole 135 is directly visible in the back view of the modified nebulizer in FIG. 9, although a joint that fuses the jacket 116 to the chimney 121 structure is shown in front of a portion of this hole 135. The side view of FIG. 10 shows the profile of the at most two small jacket holes 135. No aerosol is generated from restricted opening 118 when the small jacket hole 135 is free from obstruction. Restricted opening 118 is not visible in FIGS. 9-10.

Figure 11:
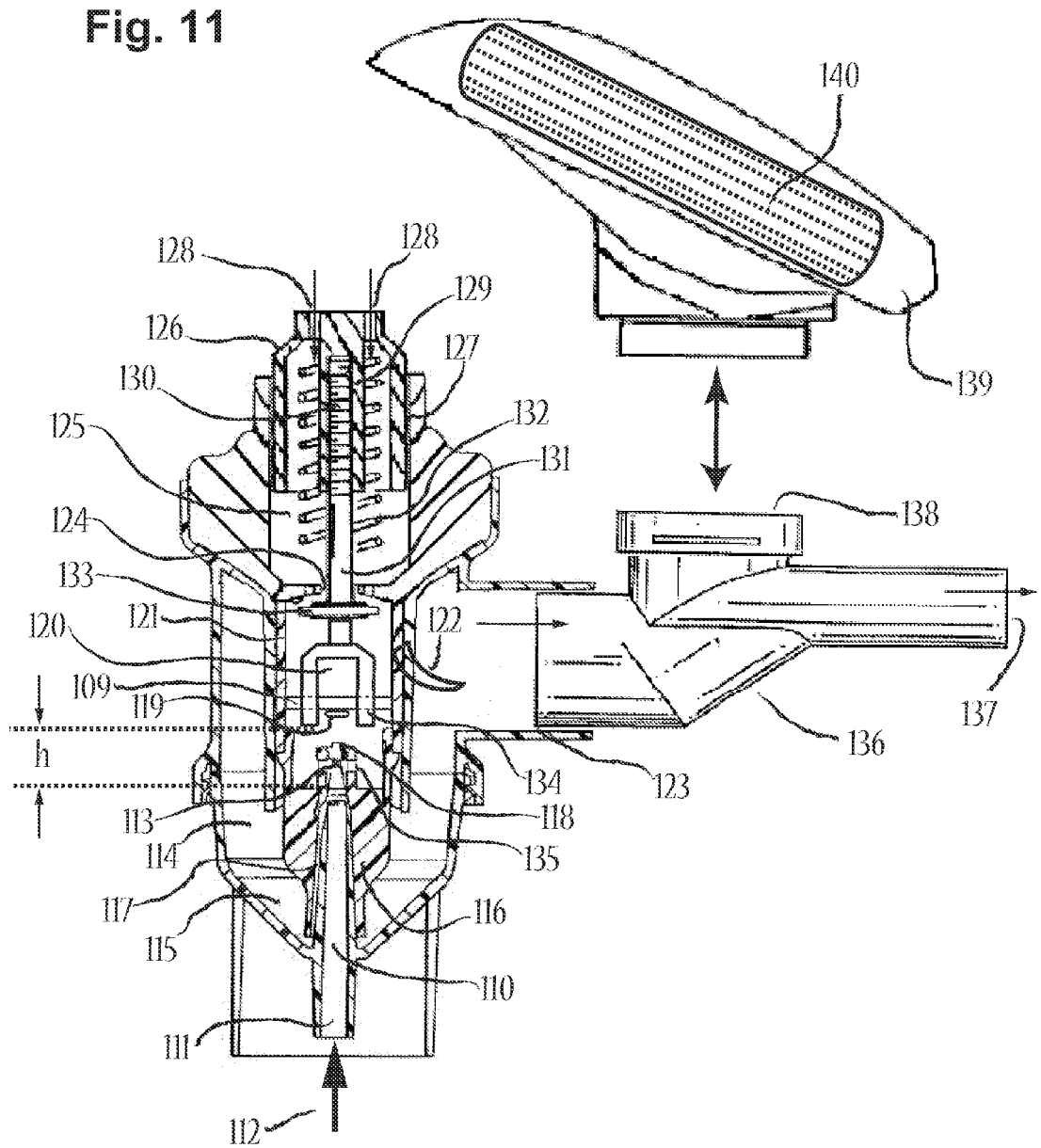
FIG. 11 is a cross-sectional side view of the modified nebulizer shown in a non-actuated state. The modification of a moveable seal 134 attached to the actuator piston of the valve is visible from this view.
Figure 12:
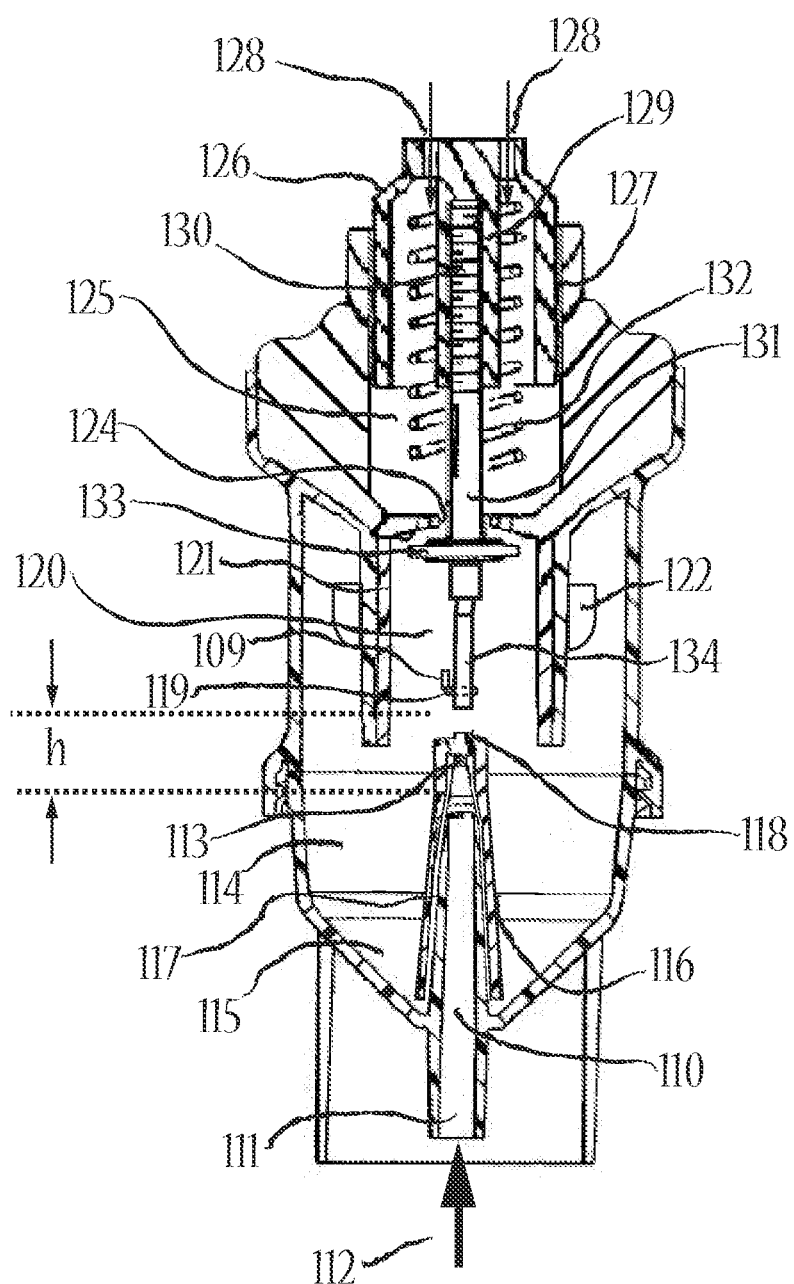
FIG. 12 is a cross-sectional back view of the modified nebulizer shown in a non-actuated state. The modification of a moveable seal 134 attached to the actuator piston of the valve is visible from this view.

Referring now to the cross-sectional views, FIG. 11 side view and FIG. 12 back view, this exemplary jet nebulizer is shown with an accompanying modification of including a movable and preferably horseshoe-shaped seal 134 that is attached to the bottom of the actuator piston. More specifically, the moveable seal is attached under the circular disc, and preferably attached to the end of thin rod 131, a portion of the rod which extends past circular disc 133.

The entire jet nozzle 110 is in a fixed position in the nebulizer housing. The entire jacket 116 is comprised of a single piece and is fixedly positioned over the jet nozzle and does not move so that the fluid-introducing gap 117 is held constant. Only the horseshoe-shaped seal 134 is moveable to flank the small jacket hole 135 of the non-moveable jacket. The horseshoe-shaped seal 134 is not a component or portion of the nozzle jacket.

Figure 13:
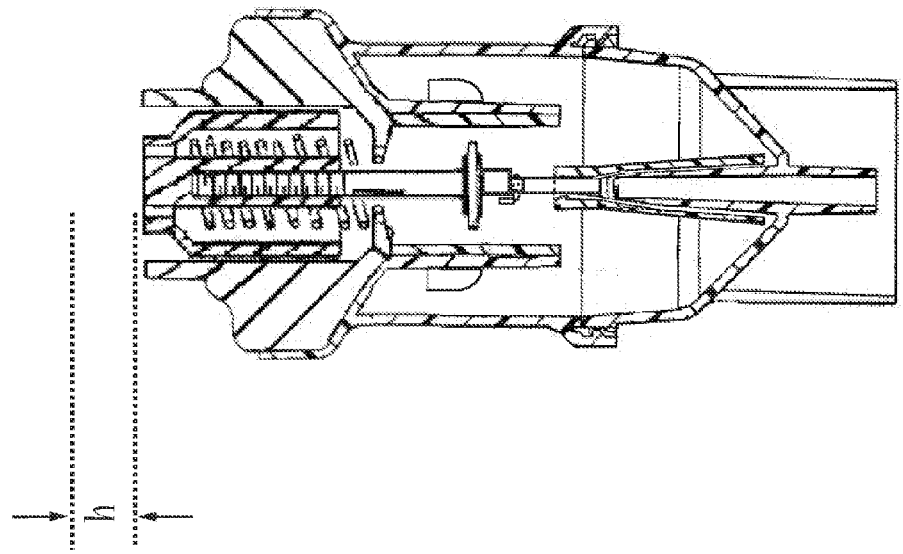
FIG. 13 is a cross-sectional back view of the modified nebulizer illustrating the adjustable negative pressure threshold valve according to an exemplary embodiment of the invention in a non-actuated, non-nebulizing state. The entire jacket 116 is fixed in position over the jet nozzle 110.
Figure 14:
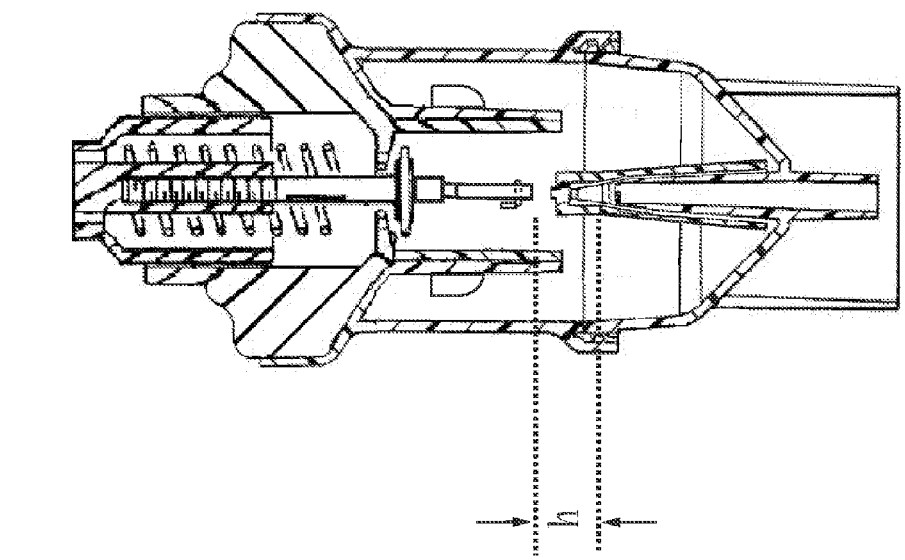
FIG. 14 is a cross-sectional back view of the modified nebulizer illustrating the adjustable negative pressure threshold valve according to an exemplary embodiment of the invention in a fully actuated nebulizing state after having moved a distance of "h" downward with moveable seal flanking the jacket tip. The entire jacket 116 remained fixed in position over the jet nozzle 110.

Referring now to FIGS. 13-14, upon a threshold level of negative pressure achieved by inhalation, the actuator piston of threshold valve 125 moves downward by a distance 'h', thereby, placing horseshoe-shaped seal 134 into a position that permits nebulization. Nebulization occurs when horseshoe-shaped seal 134 flanks small jacket hole 135 and obstructs it, so that aerosol is generated from restricted opening 118.

When negative pressure from inhalation decreases and can no longer hold the valve open, such as towards the end of inhalation, the valve closes, the piston moves upward, and the moveable seal is no longer in a position that allows nebulization. In this manner, nebulization only takes place when the user is able to inhale through this device and generate a negative pressure at least as great as the threshold required for actuation. Downward movement of the cap 126 may also signal that inhalation and nebulization are taking place.

The negative pressure threshold valve is capable of being bypassed when no actuation threshold is desired. For example, cap 126 may be unscrewed and removed from the rod 131, or manually pushed down and twisted to a locking position, which allows for continuous nebulization. Referring now to the cross-sectional side view of FIGS. 15-16, a still further modification to the exemplary embodiment of the invention is shown including a valve bypass lock pin 142 and dial lock pin port 143. The valve bypass lock pin 142 is slidably received horizontally through the upper housing of the device. Rotatable cap 126 is modified with at least one dial lock pin port 143 on its corresponding side or sides. When the rotatable cap is moved downward a distance of 'h' either manually by hand or by breath actuation of the valve, the lock pin is correctly aligned to be pushed in and slidably received by the lock pin port. The valve is bypassed and held open so that no negative pressure threshold exists until the lock pin is pulled back out to the unlocked position.

The modified jet nebulizer of FIGS. 9-14, and the modified jet nebulizer of FIGS. 15-16, according to the present invention have a variable negative pressure threshold valve that actuates in response to different negative pressures corresponding to different negative pressure threshold settings of actuation. The negative pressure threshold valve is adjustable and includes a biasing member component of the valve, the valve further including settings that change the negative pressure thresholds of actuation of the valve by changing the biasing member force of the biasing member component of the valve. The valve is able to influence nebulized aerosol delivery and allow ambient air to enter and entrain aerosol particles. In essence, the adjustable negative pressure threshold valve, which actuates in response to different negative pressures corresponding to different negative pressure threshold settings of actuation; is further structured to serve as a nebulization actuator so that nebulization is coordinated with the breathing cycle. More specifically, these modified nebulizers of the present invention have a dialable negative pressure threshold valve, the valve actuates in response to different negative pressures above 1 centimeter of water, and preferably above 3 centimeters of water, corresponding to different negative pressure threshold settings of actuation; the settings change the negative pressure thresholds of actuation of the valve by changing the biasing member force of a biasing member component of the valve when the orientation of a dialable component of the valve is changed; the valve further structured to serve as a nebulization actuator piston so that nebulization is coordinated with the breathing cycle.

Increased negative pressure threshold settings of this invention require an increased inhalation effort and can provide exercise to the muscles involved in respiration. The breathing exercise therapy provided by this nebulizer can also help maintain lung elasticity.

For patients with adequate lung function that can achieve greater inhalation effort, the different negative pressure threshold settings of this novel nebulizer can have profound effects on aerosol delivery dynamics. Aerosol generation and aerosol delivery occur when enough negative pressure builds within the device to cause actuation. After building up the necessary negative pressure required for valve actuation, aerosol is generated at the precise moment that the valve opens to allow a rapid stream of ambient air into the device for entraining and efficiently carrying out this aerosol as a bolus. Choosing different settings can allow this bolus to be sustained as a stream over different lengths of inhalation time corresponding to different negative pressures that can be sustained and selected by the patient. Moreover, by having actuation of nebulization and aerosol entrainment associated with different negative pressure threshold settings, this novel nebulizer can be used to selectively target aerosols to one or more different airway regions. In effect, aerosol actuation, entrainment, and delivery occur when one or more different airways are optimally expanded with the desired pressure for enhanced drug targeting and delivery efficiency. The nebulizer is thus adapted to selectively target aerosols to one or more different airway regions by selecting different negative pressure threshold settings of actuation of nebulization. The one or more different airway regions are chosen from the regions, including, but not limited to, the upper airways, upper respiratory tract, nasal cavity, pharynx, larynx, lower airways, lower respiratory tract, trachea, bronchi, lungs, bronchioles, deep lung, and alveoli where systemic exchange takes place.

More pharmaceuticals are being made available for inhalation. This includes pharmaceuticals that can be delivered to the systemic circulation via the pulmonary route, such as insulin. As an improved drug delivery device, the present invention can improve the delivery dynamics and targeting of these drugs. Selective targeting of aerosols to one or more different airway regions can aid in the targeting of aerosolized chemotherapies against lung cancer, including targeting an airway region having a tumor. Selective targeting of aerosols to one or more different airway regions can also have profound lifesaving and medical military applications, including biodefense to counter bioterrorism, by coating upper airways with antibiotics against anthrax or other infectious agents, or by providing anticholinergic agents to the systemic circulation via alveoli as an antidote to nerve agent exposure. The present invention also has the potential to enhance the deliverability of drug candidates in development, which has the potential to reduce drug development costs. Therefore, the present invention fulfills important unmet other needs, and has applications that transcend beyond medication delivery to asthma, COPD, and cystic fibrosis patients that have trouble breathing, and opens the way for treating countless other patients, including those with the ability to generate greater negative pressures.

The present invention is able to deliver aerosols of various substances that include, but at not limited to: unformulated active pharmaceutical ingredient, formulated active pharmaceutical ingredient, non-biological materials, biological materials, plant material or extracts, animal material or extracts, cellular material or extracts, cultured cell line material or extracts, cells, stem cells, bacterial material or extracts, fungal material or extracts, viral material or extracts, peptides, polypeptides, recombinant proteins, glycoproteins, sugars, monosaccharides, disaccharides, and polysaccharides, lipids, fatty acids and prostaglandins, cholesterol, lipoproteins, vesicles, liposomes, nutrients/supplements, holistic substances, antibodies/immunoglobulins and/or fragments thereof, water, water soluble substances, water insoluble substances, vitamins, coenzymes, enzymes, substrates, inhibitors, hormones, steroids, amino acids, neurotransmitters, cell signaling molecules, antibiotics, cellular receptors and/or receptor fragments, ion channels/ion channel fragments, ligands/ligand fragments, single stranded/double stranded nucleotides, deoxyribonucleic acids and/or ribonucleic acids, small interfering RNA, siRNA, transcription factors, transcription inhibitors, translation factors, translation inhibitors, vaccines, antihistamines, anti-inflammatory substances, cytotoxic substances, anti-toxins, anti-venoms, anticoagulants, vasodilators, bronchodilators, stimulants, anti-depressants, analgesics, anesthetics, therapeutic gases, including, but not limited to nitric oxide, nitrous oxide, hydrogen sulfide, carbon monoxide, carbon dioxide, nitrogen, cyclopropane, helium, and oxygen, diatomic molecules and gases, electrolytes, ionic substances, non-ionic substances, minerals, salts, hydrates, anhydrates, naturally occurring non-organic molecules or compounds, synthetic/modified non-organic molecules or compounds, naturally occurring organic molecules or compounds, synthetic/modified organic molecules or compounds, medical/diagnostic probes/tracers, fluorescent substances, magnetic substances, radioisotopes or radioactive substances, nanoparticles, from any phase of any of these aforementioned materials, solid phases, liquid phases, gaseous phases, polymers of any of these aforementioned materials, precursors of any of these aforementioned materials, derivatives of any of these aforementioned materials, enantiomers of any of these aforementioned materials, stereoisomers of any of these aforementioned materials, hybrid molecules of any of these aforementioned materials, combinations of any of these aforementioned materials, suspensions, mixtures/solutions of any of these aforementioned materials.

Examples of pharmaceutical aerosols that can be delivered by the present invention include, but are not limited to: acebutolol, acetaminophen, alprazolam, amantadine, amitriptyline, amoxicillin, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, insulin, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nicotine, nortriptyline, olanzapine, orphenadrine, oxycodone, paroxetine, pergolide, phenytoin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocainide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tetrahydrocannabinol, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, triamcinolene acetonide, epinephrine, and any analogues, derivatives, and combinations thereof.

Other embodiments of nebulizers within the scope of the present invention include motorized or electronic controlled adjustable negative pressure threshold valves of actuation, which employ the use of solenoid valves and pressure sensors and the necessary circuitry, buttons, and power elements to accomplish this. Other conceivable nebulizer embodiments can include handheld nebulizers that have their own built-in air compressors and power elements.

Further embodiments can include piezo-electric nebulizer generating means in addition to or instead of a jet nozzle.

Even further conceivable nebulizer embodiments can include a moveable seal that exists in a position that allows nebulization to occur until moved out of position by actuation of the valve during inhalation, so that nebulization does not occur during inhalation, but nebulization occurs during exhalation.

These other conceivable embodiments are not shown and are not meant to be limiting.

There are methods for using the nebulizers disclosed in the present invention, as well as, methods to produce the desired therapies and aerosol delivery dynamics when using the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nebulizer including:
a variable negative pressure threshold valve, the variable negative pressure threshold valve including a plurality of settings of actuation; and
means to vary the settings of actuation of the variable negative pressure threshold valve, the variable negative pressure threshold valve adapted to actuate in response to different negative pressures corresponding to different negative pressure threshold settings of actuation, the variable negative pressure threshold valve modulating flow of ambient air through the variable negative pressure threshold valve and nebulization chamber;
wherein the nebulizer is adapted to nebulize/atomize a liquid substance/solution for inhalation using compressed/pressurized gas, the nebulizer further including a liquid reservoir container defining an inner space adapted to receive a liquid therein, a jet nozzle provided through at least some of the inner space for passage of a pressurized gas entering from a gas inlet and exiting through a tapered air outlet at a jet nozzle tip, a jacket circumferentially sleeved around the jet nozzle to define a fluid-introducing gap there between, the fluid-introducing gap being in fluid communication with the inner space for passage of the liquid there through, the jacket including at least one restricted opening at a jacket tip which emits a jet, a mist-discharging conduit extending into the nebulization chamber and in fluid communication with the inner space for passage of a mist there through and aligned with the jacket in a jet-ejecting direction, an impact baffle positioned in a path of the jet to disperse nebulized particles generated as high-pressure gas atomizes the liquid leaving the at least one restricted opening of the jacket tip, at least one ambient air inlet for the mist-discharging conduit to receive ambient air, and an aerosol air outlet port for delivering aerosol to the airways of a patient.

2. The nebulizer as set forth in claim 1 wherein the nebulizer further includes a dial that is associated with the negative pressure threshold valve, the dial further adapted to change the negative pressure threshold settings of actuation when rotated by a user, the dial further including indicia to mark the different negative pressure threshold settings of actuation.

3. The nebulizer as set forth in claim 1 adapted to provide for a sustained maximal inhalation when a patient is able to sustain for a period of inhalation a negative pressure that is at least as great as the negative pressure threshold setting selected by the patient.

4. The nebulizer as set forth in claim 1 adapted to provide negative pressure threshold resistance training exercise to a patient, said negative pressure threshold resistance training exercise capable of being performed with and without simultaneous nebulized aerosol delivery.

5. A nebulizer adapted to nebulize/atomize a liquid substance/solution for inhalation using compressed/pressurized gas, the nebulizer including:
- a liquid reservoir container defining an inner space adapted to receive a liquid therein, a non-moveable jet nozzle provided through at least some of the inner space for passage of a pressurized gas entering from a gas inlet and exiting through a tapered air outlet at a jet nozzle tip, a non-moveable jacket circumferentially sleeved around the non-moveable jet nozzle to define a constant fluid-introducing gap there between, the constant fluid-introducing gap being in fluid communication with the inner space for passage of the liquid there through;
- the non-moveable jacket including at least one restricted opening at a jacket tip which emits a jet, a mist-discharging conduit of a chimney region extending into a nebulization chamber and in fluid communication with the inner space for passage of a mist there through and aligned with the non-moveable jacket in a jet-ejecting direction, an impact baffle positioned in a path of the jet to disperse nebulized particles generated as high-pressure gas atomizes the liquid leaving the at least one restricted opening of the jacket tip, at least one ambient air inlet for the mist-discharging conduit to receive ambient air, and an aerosol air outlet port for delivering aerosol to a patient;
- the non-moveable jacket further including at most two additional holes at the jacket tip, adjacent to the at least one restricted opening, when said at most two additional holes at the jacket tip are unobstructed nebulization does not take place so that aerosol is not generated from the at least one restricted opening of the jacket tip;
- the nebulizer further including a negative pressure threshold valve, the negative pressure threshold valve including a biasing member, the negative pressure threshold valve also including an actuator piston that responds to a threshold negative pressure generated by inhalation from the patient that exceeds a biasing member force of the biasing member;
- the nebulizer further including a moveable seal, non-jacket component attached to a bottom of the actuator piston;
- when said negative pressure threshold valve is actuated, the moveable seal moves downward to flank and obstruct the at most two additional holes at the jacket tip of the non-moveable jacket so that nebulization takes place while negative pressure above the threshold negative pressure is generated during inhalation, nebulization stops when the moveable seal and actuator piston return to a resting position when negative pressure drops below the threshold negative pressure as inhalation ends.

6. The nebulizer as set forth in claim 5 wherein the nebulizer is adapted to only allow ambient air to enter when the negative pressure threshold valve is actuated during inhalation.

7. The nebulizer as set forth in claim 5 wherein the nebulizer is adapted to entrain aerosol for delivery to the patient only when the negative pressure threshold valve is actuated during inhalation.

8. The nebulizer as set forth in claim 5 wherein nebulization is inhalation activated and coordinated with the breathing cycle so that an aerosol substance is conserved until/between periods of user inhalation.

9. The nebulizer as set forth in claim 5 wherein the negative pressure threshold valve is adjustable, the adjustable negative pressure threshold valve including a plurality of settings of actuation;
- the nebulizer further including a reciprocable component operatively coupled to the adjustable negative pressure threshold valve, the reciprocable component adapted to adjust the settings of actuation of the adjustable negative pressure threshold valve,
- a biasing member component of the adjustable negative pressure threshold valve including an adjustable biasing member force corresponding to the negative pressure threshold of actuation of the adjustable negative pressure threshold valve,
- the reciprocable component adapted to be dialed to adjust the settings of actuation of the adjustable negative pressure threshold valve by changing the adjustable biasing member force of the biasing member component,
- the adjustable negative pressure threshold valve adapted to actuate in response to different negative pressures corresponding to different negative pressure threshold settings of actuation; and
- the nebulizer also including a chamber operatively coupled to the adjustable negative pressure threshold valve, the chamber adapted to receive both nebulized aerosol particles and ambient air, the reciprocable component adapted to influence a nebulized aerosol delivery, the reciprocable component also adapted to allow ambient air to enter the adjustable negative pressure threshold valve and entrain aerosol particles inside the nebulizer.

10. The nebulizer as set forth in claim 9 whereby the reciprocable component operatively coupled to the adjustable negative pressure threshold valve is comprised of a rotatable cap with an integrally formed cylindrical wall slidably received through a preferably cylindrical upper region of a nebulizer housing; the rotatable cap further including one set of ambient air inlets at a top base of the rotatable cap;
- the rotatable cap further including a tubular guide extending through a portion of the rotatable cap, the tubular guide including female threads designed to receive male threads of a thin rod comprising a component of the adjustable negative pressure threshold valve so that the reciprocable component is operatively coupled to the adjustable negative pressure threshold valve;
- a biasing member component of the adjustable negative pressure threshold valve is a load calibrated, coiled spring and is positioned inside of the rotatable cap around the tubular guide and thin rod;
- the thin rod further including a circular disc fixedly attached to a bottom of the thin rod, the circular disc and thin rod comprising an actuator piston of the adjustable negative pressure threshold valve, said circular disc located within the chamber of the nebulizer, and preferably within a chimney region of the nebulizer, the nebulizer including a Venturi-like central aperture between the disc and the rotatable cap;
- the load calibrated, coiled spring puts upward pressure on rotatable cap so that circular disc is pulled against a top surface of the chimney region to block the Venturi-like central aperture and prevent ambient air from entering the Venturi-like central aperture before actuation of the adjustable negative pressure threshold valve, the load calibrated, coiled spring further including a biasing member force that is modulated by rotation of the rotatable cap so that the distance that the thin rod screws into the tubular guide of the rotatable cap changes, thereby affecting the space between the rotatable cap and the Venturi-like central aperture of the nebulizer housing, thereby changing a compression and tension of the load calibrated, coiled spring and changing a negative pressure threshold required for actuation of the adjustable negative pressure threshold valve;

the adjustable negative pressure threshold valve actuating when a negative pressure is generated by patient inhalation to surpass the biasing member force of the load calibrated, coiled spring so that the actuator piston moves downward to allow ambient air to enter the Venturi-like central aperture of the nebulizer;

actuation of the adjustable negative pressure threshold valve ceases when negative pressure generated by the patient decreases below the negative pressure threshold of the adjustable negative pressure threshold valve, and the actuator piston and adjustable negative pressure threshold valve return to a resting position.

11. The nebulizer as set forth in claim 9 wherein the negative pressure threshold valve actuates in response to different negative pressures above 1 centimeter of water, and preferably above 3 centimeters of water, corresponding to different negative pressure threshold settings of actuation.

12. The nebulizer as set forth in claim 9 that further includes marked indicia, and preferably calibrated indicia, adapted to be presented to the user and further representing the different negative pressure threshold settings for actuation of the negative pressure threshold valve, said valve further serving as a calibrated negative pressure threshold control element.

13. The nebulizer as set forth in claim 9 adapted to selectively target aerosols to one or more different airway regions by selecting different negative pressure threshold settings of actuation of nebulization, one or more different airway regions being chosen from the regions, including, but not limited to, the upper airways, upper respiratory tract, nasal cavity, pharynx, larynx, lower airways, lower respiratory tract, trachea, bronchi, lungs, bronchioles, deep lung, and alveoli where systemic exchange takes place.

14. A nebulizer adapted to nebulize/atomize a liquid substance/solution for inhalation using compressed/pressurized gas, the nebulizer including: a liquid reservoir container defining an inner space adapted to receive a liquid therein, a non-moveable jet nozzle provided through at least some of the inner space for passage of a pressurized gas entering from a gas inlet and exiting through a tapered air outlet at a jet nozzle tip, a non-moveable jacket circumferentially sleeved around the non-moveable jet nozzle to define a constant fluid-introducing gap there between, the constant fluid-introducing gap being in fluid communication with the inner space for passage of the liquid there through, the non-moveable jacket including at least one restricted opening at a jacket tip which emits a jet, a mist-discharging conduit, chimney, extending into a nebulization chamber and in fluid communication with the inner space for passage of a mist there through and aligned with the non-moveable jacket in a jet-ejecting direction, an impact baffle fixedly positioned in a path of the jet to disperse nebulized particles generated as high-pressure gas atomizes the liquid leaving the at least one restricted opening of the jacket tip, at least one aperture for the chimney to receive ambient air, and an aerosol air outlet port for delivering aerosol to t a patient;

the non-moveable jacket further including at most two additional holes at the jacket tip, adjacent to the at least one restricted opening, so that when the at most two additional holes at the jacket tip are unobstructed, nebulization does not take place so that aerosol is not generated from the at least one restricted opening of the jacket tip;

the nebulizer further including an adjustable negative pressure threshold valve operatively coupled to the nebulization chamber and chimney, the nebulization chamber adapted to receive both nebulized aerosol particles and ambient air;

the adjustable negative pressure threshold valve including a plurality of settings of actuation, the nebulizer further including a reciprocable component operatively coupled to the adjustable negative pressure threshold valve, the reciprocable component adapted to adjust the settings of actuation of the adjustable negative pressure threshold valve, the reciprocable component comprised of a rotatable cap with an integrally formed cylindrical wall slidably received through a preferably cylindrical upper region of a nebulizer housing, the rotatable cap including one set of ambient air inlets at a top base of the rotatable cap;

the rotatable cap further including a tubular guide extending through a portion of the rotatable cap, the tubular guide including female threads designed to receive male threads of a thin rod comprising a component of the adjustable negative pressure threshold valve so that the reciprocable component is operatively coupled to the adjustable negative pressure threshold valve, the thin rod further including a circular disc fixedly attached to a bottom of the thin rod, the circular disc and thin rod comprising an actuator piston of the adjustable negative pressure threshold valve, the circular disc located within the nebulization chamber of the nebulizer, and preferably within a chimney region of the nebulizer, the nebulizer including a Venturi-like central aperture between the disc and the rotatable cap;

the nebulizer further including a moveable seal associated with the actuator piston, the moveable seal preferably horseshoe-shaped, the moveable seal not a component of the non-moveable jacket, the moveable seal is attached under the circular disc, and preferably attached to an end of the thin rod, a portion of the rod which extends past the circular disc;

a load calibrated, coiled spring biasing member further comprising the adjustable negative pressure threshold valve and positioned inside of the rotatable cap around the tubular guide and thin rod, the load calibrated, coiled spring biasing member puts upward pressure on the rotatable cap so that the circular disc is pulled against a top surface of the chimney region to block the Venturi-like central aperture and prevent ambient air from entering the Venturi-like central aperture before actuation of the adjustable negative pressure threshold valve takes place;

the load calibrated, coiled spring biasing member further including an adjustable biasing member force that is modulated by rotation of the rotatable cap so that the distance that the thin rod screws into the tubular guide of the rotatable cap changes, thereby affecting the space between the rotatable cap and the Venturi-like central aperture of the chimney, and thereby changing a compression and tension of the load calibrated, coiled spring biasing member and changing a negative pressure threshold required for actuation of the adjustable negative pressure threshold valve, the reciprocable component adapted to adjust the settings of actuation of the adjustable negative pressure threshold valve by changing the adjustable biasing member force of the biasing member component; the adjustable negative pressure threshold valve adapted to actuate in response to different negative pressures corresponding to different negative pressure threshold settings of actuation above 1 centimeter of water, and preferably above 3 centimeters of water, the adjustable negative pressure threshold valve actuates when a negative pressure is generated by patient inhalation to surpass the adjustable biasing member force of the load calibrated, coiled spring biasing member, so that the actuator piston moves downward, said downward movement of the actuator piston allowing ambient air to enter the Venturi-like central aperture of the nebulizer, said ambient air coming from the ambient air inlet of the reciprocable component of the adjustable negative pressure threshold valve, said downward movement of the actuator piston during actuation also moving the moveable seal downward to flank and obstruct the at most two additional holes at the jacket tip of the non-moveable jacket so that nebulization takes place while negative pressure above the negative pressure threshold is generated during inhalation, the reciprocable component and the adjustable negative pressure threshold valve adapted to influence nebulized aerosol delivery by allowing ambient air to enter the nebulization chamber and entrain aerosol particles when nebulization is actuated;

actuation of the adjustable negative pressure threshold valve ceasing when the negative pressure generated by the patient decreases below the negative pressure threshold of the adjustable negative pressure threshold valve, as inhalation ends, so that the actuator piston of the adjustable negative pressure threshold valve and associated moveable seal return to a resting position and the at most two additional holes at the jacket tip are unobstructed again and nebulization stops, said nebulization coordinated with the patient's breathing cycle.

* * * * *